(12) United States Patent
Glossop

(10) Patent No.: US 7,805,269 B2
(45) Date of Patent: Sep. 28, 2010

(54) DEVICE AND METHOD FOR ENSURING THE ACCURACY OF A TRACKING DEVICE IN A VOLUME

(75) Inventor: Neil David Glossop, Toronto (CA)

(73) Assignee: Philips Electronics Ltd, Vancouver, British Columbia (CA)

( * ) Notice: Subject to any disclaimer, the term of this patent is extended or adjusted under 35 U.S.C. 154(b) by 135 days.

(21) Appl. No.: 11/271,966

(22) Filed: Nov. 14, 2005

(65) Prior Publication Data

US 2006/0122497 A1 Jun. 8, 2006

Related U.S. Application Data

(60) Provisional application No. 60/626,947, filed on Nov. 12, 2004.

(51) Int. Cl.
*G01C 25/00* (2006.01)
(52) U.S. Cl. .......................................................... 702/94
(58) Field of Classification Search .................... 702/94
See application file for complete search history.

(56) References Cited

U.S. PATENT DOCUMENTS

| | | | |
|---|---|---|---|
| 3,021,842 A | 2/1962 | Flood | |
| 4,080,706 A | 3/1978 | Heilman et al. | 29/173 |
| 4,279,252 A | 7/1981 | Martin | 128/349 R |
| 4,697,595 A | 10/1987 | Breyer et al. | 128/660 |
| 4,722,056 A | 1/1988 | Roberts et al. | 364/413 |
| 4,777,951 A | 10/1988 | Cribier et al. | 128/344 |
| 4,887,606 A | 12/1989 | Yock et al. | 128/662.05 |
| 4,895,168 A | 1/1990 | Machek | 128/772 |
| 4,935,019 A | 6/1990 | Papp, Jr. | 604/362 |
| 4,961,433 A | 10/1990 | Christian | 128/772 |
| 5,014,708 A | 5/1991 | Hayashi et al. | 128/653 R |
| 5,042,486 A | 8/1991 | Pfeiler et al. | 128/653 R |
| 5,045,080 A | 9/1991 | Dyer et al. | 604/362 |
| 5,085,659 A | 2/1992 | Rydell | 606/47 |

(Continued)

FOREIGN PATENT DOCUMENTS

AU   6367896   2/1997

(Continued)

OTHER PUBLICATIONS

TRA002—Solomon, Stephen B., et al., "Three-Dimensional CT-Guided Bronchoscopy with a Real-Time Electromagnetic Position Sensor: A Comparison of Two Image Registration Methods", *Chest*, vol. 118, No. 6, Dec. 2000, pp. 1783-1787.

(Continued)

*Primary Examiner*—Aditya Bhat

(57) ABSTRACT

The invention provides a system and method for testing and correcting the accuracy of a tracking device in a volume using an accuracy device. The invention may include placing a rigid object into an experimental volume and sampling position and orientation information regarding one or more position indicating elements at known positions relative to a frame of reference of the tracking device. The position and orientation information may then be compared to known baseline position and orientation information. If a difference between the experimental position and orientation information and the baseline position and orientation information exceeds a predetermined threshold, a correction map enabling adjustment of the tracking device to correct for the distortion in the experimental volume may be generated, and the tracking device may be adjusted accordingly.

32 Claims, 8 Drawing Sheets

U.S. PATENT DOCUMENTS

| | | | |
|---|---|---|---|
| 5,116,345 A | 5/1992 | Jewell et al. | 606/130 |
| 5,187,658 A | 2/1993 | Cline et al. | 364/413.13 |
| 5,204,625 A | 4/1993 | Cline et al. | 324/306 |
| 5,207,675 A | 5/1993 | Canady | 606/40 |
| 5,211,165 A | 5/1993 | Dumoulin et al. | 128/653.1 |
| 5,221,283 A | 6/1993 | Chang | 606/130 |
| 5,247,935 A | 9/1993 | Cline et al. | 128/653.2 |
| 5,251,127 A | 10/1993 | Raab | 364/413.13 |
| 5,251,635 A | 10/1993 | Dumoulin et al. | 128/653.2 |
| 5,255,680 A | 10/1993 | Darrow et al. | 128/653.1 |
| 5,265,610 A | 11/1993 | Darrow et al. | 128/653.1 |
| 5,271,400 A | 12/1993 | Dumoulin et al. | 128/653.2 |
| 5,275,165 A | 1/1994 | Ettinger et al. | 128/653.2 |
| 5,290,266 A | 3/1994 | Rohling et al. | 604/272 |
| 5,291,010 A | 3/1994 | Tsuji | 250/208.1 |
| 5,291,890 A | 3/1994 | Cline et al. | 128/653.2 |
| 5,304,933 A | 4/1994 | Vavrek et al. | 324/318 |
| 5,305,203 A | 4/1994 | Raab | 364/413.13 |
| 5,307,812 A | 5/1994 | Hardy et al. | 128/653.2 |
| 5,318,025 A | 6/1994 | Dumoulin et al. | 128/653.2 |
| 5,323,779 A | 6/1994 | Hardy et al. | 128/653.2 |
| 5,327,884 A | 7/1994 | Hardy et al. | 128/653.2 |
| 5,353,808 A | 10/1994 | Viera | 128/772 |
| 5,365,927 A | 11/1994 | Roemer et al. | 128/653.2 |
| 5,368,031 A | 11/1994 | Cline et al. | 128/653.2 |
| 5,368,032 A | 11/1994 | Cline et al. | 128/653.2 |
| 5,377,678 A | 1/1995 | Dumoulin et al. | 128/653.1 |
| 5,383,454 A | 1/1995 | Bucholz | 128/653.1 |
| 5,383,465 A | 1/1995 | Lesny et al. | 128/662.05 |
| 5,386,828 A | 2/1995 | Owens et al. | 128/653.1 |
| 5,389,101 A | 2/1995 | Heilbrun et al. | 606/130 |
| 5,391,199 A | 2/1995 | Ben-Haim | 607/122 |
| 5,396,905 A | 3/1995 | Newman et al. | 128/849 |
| 5,400,383 A | 3/1995 | Yassa et al. | 378/98.2 |
| 5,437,277 A | 8/1995 | Dumoulin et al. | 128/653.2 |
| 5,443,066 A | 8/1995 | Dumoulin et al. | 128/653.1 |
| 5,443,068 A | 8/1995 | Cline et al. | 128/653.5 |
| 5,445,150 A | 8/1995 | Dumoulin et al. | 128/653.1 |
| 5,465,732 A | 11/1995 | Abele | 128/772 |
| 5,480,382 A | 1/1996 | Hammerslag et al. | 604/95 |
| 5,490,840 A | 2/1996 | Uzgiris et al. | 604/22 |
| 5,493,598 A | 2/1996 | Yassa et al. | 378/98.2 |
| 5,526,812 A | 6/1996 | Dumoulin et al. | 128/653.1 |
| 5,526,814 A | 6/1996 | Cline et al. | 128/653.2 |
| 5,558,091 A | 9/1996 | Acker et al. | 128/653.1 |
| 5,603,318 A | 2/1997 | Heilbrun et al. | 128/630 |
| 5,645,065 A | 7/1997 | Shapiro et al. | 128/653.1 |
| 5,646,524 A | 7/1997 | Gilboa | 324/207.17 |
| 5,646,525 A | 7/1997 | Gilboa | 324/207.17 |
| 5,647,373 A | 7/1997 | Paltieli | 128/749 |
| 5,705,014 A | 1/1998 | Schenck et al. | 156/272.4 |
| 5,713,858 A | 2/1998 | Heruth et al. | 604/93 |
| 5,715,166 A | 2/1998 | Besl et al. | 364/474.24 |
| 5,715,822 A | 2/1998 | Watkins et al. | 128/653.5 |
| 5,740,802 A | 4/1998 | Nafis et al. | 128/653.1 |
| 5,749,835 A | 5/1998 | Glantz | 600/424 |
| 5,769,790 A | 6/1998 | Watkins et al. | 600/439 |
| 5,769,861 A | 6/1998 | Vilsmeier | 606/130 |
| 5,848,969 A | 12/1998 | Panescu et al. | 600/462 |
| 5,857,032 A | 1/1999 | Wang et al. | 382/154 |
| 5,868,673 A | 2/1999 | Vesely | 600/407 |
| 5,873,845 A | 2/1999 | Cline et al. | 601/3 |
| 5,880,976 A | 3/1999 | DiGioia, III et al. | 364/578 |
| 5,931,786 A | 8/1999 | Whitmore, III et al. | 600/459 |
| 5,944,023 A | 8/1999 | Johnson et al. | 128/899 |
| 5,978,696 A | 11/1999 | VomLehn et al. | 600/411 |
| 5,987,960 A * | 11/1999 | Messner et al. | 73/1.79 |
| 6,016,439 A | 1/2000 | Acker | 600/411 |
| 6,036,682 A | 3/2000 | Lange et al. | 604/529 |
| 6,073,043 A * | 6/2000 | Schneider | 600/424 |
| 6,097,978 A | 8/2000 | Demarais et al. | 600/429 |
| 6,106,476 A | 8/2000 | Corl et al. | 600/486 |
| 6,141,576 A | 10/2000 | Littmann et al. | 600/381 |
| 6,147,480 A * | 11/2000 | Osadchy et al. | 324/67 |
| 6,165,184 A | 12/2000 | Verdura et al. | 606/148 |
| 6,188,355 B1 | 2/2001 | Gilboa | 342/448 |
| 6,196,980 B1 | 3/2001 | Akerfeldt et al. | 600/585 |
| 6,203,493 B1 | 3/2001 | Ben-Haim | 600/117 |
| 6,203,543 B1 | 3/2001 | Glossop | 606/60 |
| 6,205,411 B1 | 3/2001 | DiGioia, III et al. | 703/11 |
| 6,210,339 B1 | 4/2001 | Kiepen et al. | 600/486 |
| 6,216,029 B1 | 4/2001 | Paltieli | 600/427 |
| 6,226,543 B1 | 5/2001 | Gilboa et al. | 600/407 |
| 6,233,476 B1 | 5/2001 | Strommer et al. | 600/424 |
| 6,235,038 B1 | 5/2001 | Hunter et al. | 606/130 |
| 6,241,690 B1 | 6/2001 | Burkett et al. | 600/585 |
| 6,266,551 B1 | 7/2001 | Osadchy et al. | 600/424 |
| 6,266,552 B1 | 7/2001 | Slettenmark | 600/424 |
| 6,272,370 B1 | 8/2001 | Gillies et al. | 600/411 |
| 6,272,371 B1 | 8/2001 | Shlomo | 600/424 |
| 6,285,898 B1 | 9/2001 | Ben-Haim | 600/374 |
| 6,285,903 B1 | 9/2001 | Rosenthal et al. | 600/433 |
| 6,288,785 B1 | 9/2001 | Frantz et al. | 356/614 |
| 6,308,089 B1 | 10/2001 | von der Ruhr et al. | 600/338 |
| 6,314,310 B1 * | 11/2001 | Ben-Haim et al. | 600/424 |
| 6,317,621 B1 | 11/2001 | Graumann et al. | 600/424 |
| 6,332,089 B1 | 12/2001 | Acker et al. | 600/424 |
| 6,336,906 B1 | 1/2002 | Hammarstrom et al. | 600/585 |
| 6,338,716 B1 | 1/2002 | Hossack et al. | 600/459 |
| 6,356,783 B1 | 3/2002 | Hubbard, Jr. | 600/546 |
| 6,380,732 B1 | 4/2002 | Gilboa | 324/207.17 |
| 6,381,485 B1 | 4/2002 | Hunter et al. | 600/407 |
| 6,383,174 B1 | 5/2002 | Eder | 606/1 |
| 6,385,482 B1 | 5/2002 | Boksberger et al. | 600/424 |
| 6,427,079 B1 | 7/2002 | Schneider et al. | 600/424 |
| 6,442,417 B1 | 8/2002 | Shahidi et al. | 600/429 |
| 6,468,265 B1 | 10/2002 | Evans et al. | 606/1 |
| 6,473,635 B1 | 10/2002 | Rasche | 600/428 |
| 6,484,118 B1 | 11/2002 | Govari | 702/150 |
| 6,493,589 B1 | 12/2002 | Medhkour et al. | 607/99 |
| 6,498,944 B1 | 12/2002 | Ben-Haim et al. | 600/407 |
| 6,499,488 B1 | 12/2002 | Hunter et al. | 128/899 |
| 6,500,114 B1 | 12/2002 | Petitto et al. | 600/156 |
| 6,512,958 B1 | 1/2003 | Swoyer et al. | 607/117 |
| 6,529,758 B2 | 3/2003 | Shahidi | 600/407 |
| 6,547,782 B1 | 4/2003 | Taylor | 606/14 |
| 6,558,333 B2 | 5/2003 | Gilboa et al. | 600/466 |
| 6,574,492 B1 | 6/2003 | Ben-Haim et al. | 600/374 |
| 6,574,498 B1 | 6/2003 | Gilboa | 600/424 |
| 6,580,938 B1 | 6/2003 | Acker | 600/424 |
| 6,585,654 B2 | 7/2003 | White et al. | 600/463 |
| 6,588,333 B1 | 7/2003 | Homer et al. | 101/32 |
| 6,591,127 B1 | 7/2003 | McKinnon | 600/411 |
| 6,591,129 B1 | 7/2003 | Ben-Haim et al. | 600/424 |
| 6,593,884 B1 | 7/2003 | Gilboa et al. | 342/448 |
| 6,615,155 B2 | 9/2003 | Gilboa | 702/150 |
| 6,619,838 B2 | 9/2003 | Bencini et al. | 378/190 |
| 6,628,987 B1 | 9/2003 | Hill et al. | 607/9 |
| 6,690,963 B2 | 2/2004 | Ben-Haim et al. | 600/424 |
| 6,702,780 B1 | 3/2004 | Gilboa et al. | 604/95.04 |
| 6,711,429 B1 | 3/2004 | Gilboa et al. | 600/407 |
| 6,719,700 B1 | 4/2004 | Willis | 600/462 |
| 6,735,471 B2 | 5/2004 | Hill et al. | 607/2 |
| 6,748,112 B1 | 6/2004 | Nguyen et al. | 382/203 |
| 6,753,873 B2 | 6/2004 | Dixon et al. | 345/542 |
| 6,782,287 B2 | 8/2004 | Grzeszczuk et al. | 600/424 |
| 6,783,536 B2 | 8/2004 | Vilsmeier et al. | 606/130 |
| 6,785,571 B2 | 8/2004 | Glossop | 600/424 |
| 6,788,967 B2 | 9/2004 | Ben-Haim et al. | 600/424 |
| 6,792,303 B2 * | 9/2004 | Taimisto | 600/424 |
| 6,893,429 B2 | 5/2005 | Petersen | 604/537 |
| 6,895,268 B1 | 5/2005 | Rahn et al. | 600/429 |
| 6,916,290 B2 | 7/2005 | Hedengren et al. | 600/549 |
| 7,085,400 B1 * | 8/2006 | Holsing et al. | 382/103 |

| | | | |
|---|---|---|---|
| 7,386,339 B2 | 6/2008 | Strommer et al. | 600/424 |
| 7,570,791 B2 * | 8/2009 | Frank et al. | 382/132 |
| 2001/0008972 A1 | 7/2001 | Gielen | 607/45 |
| 2001/0011175 A1 | 8/2001 | Hunter et al. | 606/130 |
| 2001/0031919 A1 | 10/2001 | Strommer et al. | 600/424 |
| 2001/0031985 A1 | 10/2001 | Gilboa et al. | 607/1 |
| 2001/0036245 A1 | 11/2001 | Kienzle, III et al. | 378/4 |
| 2001/0038354 A1 | 11/2001 | Gilboa | 342/450 |
| 2001/0039419 A1 | 11/2001 | Francischelli et al. | 606/42 |
| 2001/0047133 A1 | 11/2001 | Gilboa et al. | 600/429 |
| 2002/0005719 A1 | 1/2002 | Gilboa et al. | 324/309 |
| 2002/0038102 A1 | 3/2002 | McFarlin et al. | 604/30 |
| 2002/0042571 A1 | 4/2002 | Gilboa et al. | 600/429 |
| 2002/0049375 A1 | 4/2002 | Strommer et al. | 600/407 |
| 2002/0049451 A1 | 4/2002 | Parmer et al. | 606/108 |
| 2002/0062203 A1 | 5/2002 | Gilboa | 702/150 |
| 2002/0074005 A1 | 6/2002 | Hogg et al. | 128/899 |
| 2002/0087101 A1 | 7/2002 | Barrick et al. | 600/587 |
| 2002/0143317 A1 | 10/2002 | Glossop | 604/529 |
| 2002/0156363 A1 | 10/2002 | Hunter et al. | 600/410 |
| 2002/0156417 A1 | 10/2002 | Rich et al. | 604/65 |
| 2002/0165448 A1 * | 11/2002 | Ben-Haim et al. | 600/424 |
| 2002/0165468 A1 | 11/2002 | Tolkowsky et al. | 600/587 |
| 2003/0018251 A1 | 1/2003 | Solomon | 600/427 |
| 2003/0021455 A1 | 1/2003 | Dixon et al. | 382/132 |
| 2003/0028233 A1 | 2/2003 | Vardi et al. | 623/1.11 |
| 2003/0030004 A1 | 2/2003 | Dixon et al. | 250/370.09 |
| 2003/0074011 A1 | 4/2003 | Gilboa et al. | 606/130 |
| 2003/0092988 A1 | 5/2003 | Makin | 600/439 |
| 2003/0114778 A1 | 6/2003 | Vilsmeier et al. | 600/585 |
| 2003/0114846 A1 | 6/2003 | Fuimaono et al. | 606/41 |
| 2003/0130576 A1 | 7/2003 | Seeley et al. | 600/426 |
| 2003/0171680 A1 | 9/2003 | Paltieli | 600/459 |
| 2003/0171739 A1 | 9/2003 | Murphy et al. | 606/1 |
| 2003/0208102 A1 | 11/2003 | Gilboa | 600/41 |
| 2003/0208296 A1 | 11/2003 | Brisson et al. | 700/117 |
| 2003/0216639 A1 | 11/2003 | Gilboa et al. | 600/424 |
| 2003/0220557 A1 | 11/2003 | Cleary et al. | 600/409 |
| 2004/0019274 A1 * | 1/2004 | Galloway et al. | 600/425 |
| 2004/0024309 A1 | 2/2004 | Ferre et al. | 600/424 |
| 2004/0034297 A1 | 2/2004 | Darrow et al. | 600/407 |
| 2004/0034300 A1 | 2/2004 | Verard et al. | 600/424 |
| 2004/0036867 A1 | 2/2004 | Jedamzik et al. | 356/243.1 |
| 2004/0077942 A1 | 4/2004 | Hall et al. | 600/428 |
| 2004/0078036 A1 | 4/2004 | Keidar | 606/41 |
| 2004/0097804 A1 | 5/2004 | Sobe | 600/424 |
| 2004/0097805 A1 | 5/2004 | Verard et al. | 600/428 |
| 2004/0097806 A1 | 5/2004 | Hunter et al. | 600/434 |
| 2004/0138548 A1 | 7/2004 | Strommer et al. | 600/407 |
| 2004/0143188 A1 | 7/2004 | Barzell et al. | 600/439 |
| 2004/0147837 A1 | 7/2004 | Macaulay et al. | 600/424 |
| 2004/0147939 A1 | 7/2004 | Rabkin et al. | 606/108 |
| 2004/0158146 A1 | 8/2004 | Mate et al. | 600/427 |
| 2004/0221853 A1 | 11/2004 | Miller | 128/207.14 |
| 2004/0234933 A1 | 11/2004 | Dawson et al. | 434/262 |
| 2004/0249267 A1 | 12/2004 | Gilboa | 600/424 |
| 2004/0254458 A1 | 12/2004 | Govari | 600/437 |
| 2005/0033149 A1 | 2/2005 | Strommer et al. | 600/407 |
| 2005/0038337 A1 | 2/2005 | Edwards | 600/424 |
| 2005/0049520 A1 | 3/2005 | Nakao | 600/562 |
| 2005/0054900 A1 | 3/2005 | Mawn et al. | 600/156 |
| 2005/0059886 A1 | 3/2005 | Webber | 600/426 |
| 2005/0085715 A1 | 4/2005 | Dukesherer et al. | 600/424 |
| 2005/0085720 A1 | 4/2005 | Jascob et al. | 600/424 |
| 2005/0085793 A1 | 4/2005 | Glossop | 604/529 |
| 2005/0107688 A1 | 5/2005 | Strommer | 600/424 |
| 2005/0182295 A1 | 8/2005 | Soper et al. | 600/117 |
| 2005/0182319 A1 | 8/2005 | Glossop | 600/424 |
| 2005/0228270 A1 | 10/2005 | Lloyd et al. | 600/424 |
| 2006/0147100 A1 | 7/2006 | Fitzpatrick | 382/131 |
| 2007/0032862 A1 | 2/2007 | Weber et al. | 623/1.34 |

FOREIGN PATENT DOCUMENTS

| | | |
|---|---|---|
| AU | 722539 | 8/2000 |
| BR | 9609484 | 12/1999 |
| CA | 2226938 | 2/1997 |
| DE | 69420228 D | 9/1999 |
| DE | 69420228 T | 4/2000 |
| DE | 19845267 C1 | 5/2000 |
| EP | 0 845 959 | 6/1998 |
| EP | 0 654 244 | 8/1999 |
| EP | 1 466 552 | 10/2004 |
| IL | 0107523 | 1/2000 |
| IL | 0114610 | 7/2000 |
| JP | 10-277047 | 10/1998 |
| JP | 2000500031 T | 1/2000 |
| JP | 2005152463 | 6/2005 |
| WO | WO 97/03609 | 2/1997 |
| WO | WO 98/56295 | 12/1998 |
| WO | WO 00/22904 | 4/2000 |

OTHER PUBLICATIONS

TRA003—Solomon, Stephen B., et al., "Real-Time Cardiac Catheter Navigation on Three-Dimensional CT Images", *Journal of Interventional Cardiac Electrophysiology*, vol. 8, 2003, pp. 27-3.
TRA004—Palti-Wasserman, Daphna, et al., "Identifying and Tracking a Guide Wire in the Coronary Arteries During Angioplasty from X-Ray Images", *IEEE Transactions on Biomedical Engineering*, vol. 44, No. 2, Feb. 1997, pp. 152-164.
TRA005—Baert, Shirley A. M., et al., "Endpoint Localization in Guide Wire Tracking During Endovascular Interventions", *Academic Radiology*, vol. 10, No. 12, Dec. 2003, pp. 1424-1432.
TRA006—Baert, Shirley A. M., et al., "Three-Dimensional Guide-Wire Reconstruction from Biplane Image Sequences for Integrated Display in 3-D Vasculature", *IEEE Transactions on Medical Imaging*, vol. 22, No. 10, Oct. 2003, pp. 1252-1258.
TRA007—Baert, Shirley A. M., et al., "Guide-Wire Tracking During Endovascular Interventions", *IEEE Transactions on Medical Imaging*, vol. 22, No. 8, Aug. 2003, pp. 965-972.
TRA008—Kobashi, Keiji, et al., "A New Biomechanical Model Based Approach on Brain Shift Compensation", *MICCAI 2003*, LNCS 2878, 2003, pp. 59-66.
TRA009—Timinger, Holger, et al., "Motion Compensation for Interventional Navigation on 3D Static Roadmaps Based on an Affine Model and Gating", *Physics in Medicine and Biology*, vol. 49, 2004, pp. 719-732.
TRA010—Lorigo, Liana M., et al., "Curves: Curve Evolution for Vessel Segmentation", *Medical Image Analysis*, vol. 5, 2001, pp. 195-206 (pp. 1-14).
TRA011—Chassat, Fabrice, et al., "Experimental Protocol of Accuracy Evaluation of 6-D Localizers for Computer-Integrated Surgery: Application to Four Optical Localizers", *MICCAI 98*, vol. 1496, Oct. 1998, Cambridge, Massachusetts U.S.A., p. 277-284.
TRA012—Tsai, Roger Y., "A Versatile Camera Calibration Technique for High-Accuracy 3D Machine Vision Metrology Using Off-the-Shelf TV Cameras and Lenses", *IEEE Journal of Robotics and Automation*, vol. RA-3, No. 4, Aug. 1987, pp. 323-344.
TRA013—"Semi-Automatic Registration for Image Guided Surgery", Traxtal poster presented at CAOS '99 (Computer Assisted Orthopaedic Surgery, 4th International Symposium), MICCAI, Mar. 17-19, 1999, Davos, Switzerland, 1 page.
TRA014—Wu, Xiaohui, et al., "A Direction Space Interpolation Technique for Calibration of Electromagnetic Surgical Navigation Systems", Lecture Notes in Computer Science Medical Image Computing and Computer-Assisted Intervention, *MICCAI 2003*, LNCS 2879, Publisher: Springer-Verlag Heidelberg, 2003, pp. 215-222.
TRA015—Livyatan, Harel, "Calibration and Gradient-Based Rigid Registration of Fluoroscopic X-raysto CT, for intra Operative Navigation", Master of Science Thesis, supervised by Prof. Leo Joskowicz, School of Computer Science and Engineering, The Hebrew University of Jerusalem, Israel, Jul. 27, 2003, 92 pages.

TRA016—SuperDimension, Ltd, web page, updated in Sep. 2005, 1 page.

TRA017—Schweikard, Achim, et al., "Robotic Motion Compensation for Respiratory Movement During Radiosurgery", *Computer Aided Surgery*, vol. 5, 2000, pp. 263-277.

TRA018—Solomon, Stephen B., et al., "Real-Time Bronchoscope Tip Localization Enables Three-Dimensional CT Image Guidance for Transbronchial Needle Aspiration in Swine", *Chest*, vol. 114, No. 5, Nov. 1998, pp. 1405-1410.

TRA019—Ellsmere, James, et al., "A Navigation System for Augmenting Laparscopic Ultrasound", Center for Integration of Medicine and Innovative Technology, Cambridge, Massachusetts, 8 pages.

TRA020—Hofstetter, R., et al., "Fluoroscopy Based Surgical Navigation—Concept and Clinical Applications", Maurice E. Muller Institute for Biometrics, University of Bern, Switzerland, 1997, 3 pages.

TRA021—Tapper, Michael, et al., "Problems Encountered in the Implementation of Tsai's Algorithm for Camera Calibration", *Proc. 2002 Australasian Conference on Robotics and Automation*, Auckland, Nov. 27-29, 2002, pp. 66-70.

TRA022—Summers, Ronald M., et al., "Colonic Polyps: Complementary Role of Computer-Aided Detection in CT Colonography", *Radiology*, vol. 225, No. 2, Nov. 2002, pp. 391-399.

TRA023—Hara, A. K., et al., "Reducing Data Size and Radiation Dose for CT Colongraphy", *AJR*, vol. 168, May 1997, pp. 1181-1184.

TRA001—Tanase, Dafina, et al., "Magnetic Sensors for Use on Guide Wires or Catheters", in *SeSens* 2001, in press 2002, pp. 868-872.

TRA024—Knaan, Dotan, et al., Effective Intensity-Based 2D/3D Rigid Registration Between Fluoroscopic X-Ray and CT, *MICCAI*, vol. 1, 2003, pp. 351-358.

TRA025—Gee, A. H., et al., "3D Ultrasound Probe Calibration Without a Position Sensor", CUED/F-INFENG/TR 488, University of Cambridge, Department of Engineering, Sep. 2004, 21 pages.

TRA026—Lindseth, Frank, et al., "Probe Calibration for Freehand 3D Ultrasound Reconstruction and Surgical Navigation", Dec. 2002, 27 pages.

TRA027—Fuchs, Henry et al., "Towards Performing Ultrasound-Guided Needle Biopsies from Within a Head-Mounted Display", University of North Carolina, Department of Computer Science, 1996, 10 pages; [Lecture Notes in Computer Science; vol. 1131 archive Proceedings of the 4th International Conference on Visualization in Biomedical Computing table of contents, pp. 591-600 Year of Publication: 1996, ISBN:3-540-61649-7; Hamburg, Germany, Sep. 22-25, 1996).].

TRA028—Henry Fuchs, Andrei State, Mark A. Livingston, William F. Garrett, Gentaro Hirota, Mary Whitton and Etta D. Pisano (MD). "Virtual Environments Technology to Aid Needle Biopsies of the Breast: An Example of Real-Time Data Fusion." Proceedings of Medicine Meets Virtual Reality:4 (Jan. 17-20, 1996, San Diego, California), IOS Press, Amsterdam, Jan. 1996.

TRA029—RITA StarBurst Soft Tissue Access System and RITA StarBurst Hard Tissue Access System, http://www.ritamedical.com, Rita Medical Systems, Inc., copyright 2002, , 8 pages.

TRA030—Cool-tip RF Tissue Ablation System, Cool-tip RF System, and Cool-tip Electrodes, http://www.valleylab.com/static/cooltip/products.html, Valleylab, copyright 2004, 4 pages.

TRA031—LeVeen Needle Electrode, Boston Scientific, printed from http://www.bostonscientific.com/med_specialty/deviceDetail.jhtml?task=tskBasicDevice..., printed on Sep. 13, 2004, 1 page.

TRA032—Bradford J. Wood et al., "Navigation with Electromagnetic Tracking for Interventional Radiology Procedures: A Feasibility Study", Laboratory Investigations, *Journal of Vasc. Interv. Radiol.*, vol. 16, 2005, pp. 493-505.

* cited by examiner

DEVICE AND METHOD FOR ENSURING THE ACCURACY OF A TRACKING DEVICE IN A VOLUME

RELATED APPLICATIONS

This application claims priority to U.S. Provisional Patent Application Ser. No. 60/626,947, filed Nov. 12, 2004, which is hereby incorporated by reference herein in its entirety.

FIELD OF THE INVENTION

This invention relates to a device and method for ensuring the accuracy of a tracking device in a volume

BACKGROUND OF THE INVENTION

When performing image guided surgery using tracking devices, the fields set up by these tracking devices may be affected through the interaction of metal and other conductors with position sensors (hereinafter "position indicating elements") associated with the tracking devices. This is because conductors alter the way in which these fields are produced, causing field lines to bend and otherwise influence the way in which the field generator of the tracking device sets up a field in a "measurement volume." In general, the conductive material, the shape of the conductive material, as well as the orientation and location of the conductive material relative to the field generator and detector, are all important in assessing the interaction of the conductive material with a tracking device such as, for example, a magnetic tracking device.

In addition to distortions caused by metal objects and conductors, stray fields introduced by electrical or electromagnetic devices may also alter the measurement field of a tracking device. All of these factors may result in an alteration of the accuracy with which the tracking device reports position and orientation information regarding its associated position indicating elements.

Furthermore, tracking devices and their associated field generators may undergo various forms of damage over their lifetime that may affect their accuracy. Damage may occur, for example, from mechanical sources such as impacts, electrical sources such as high voltages, and/or magnetic sources such as high ambient magnetic fields. Normal aging of components may also affect the accuracy of a tracking device.

Suppliers of tracking equipment have adopted a variety of techniques to mitigate the effects described above and to ensure the fields produced by their systems are uniform and accurate. However, these techniques are not always adequate or sufficient. For example, these methods may be complicated and time consuming or may require specialized equipment. They may also not be appropriate to assess the particular operating environment that the tracking equipment may be used in. These and other problems exist.

SUMMARY OF THE INVENTION

The invention addresses these and other problems by providing systems and methods for ensuring the accuracy of a tracking device that provides position and orientation information of one or more position indicating elements in a volume and methods for use thereof. In one embodiment of the invention, a system for ensuring the accuracy of a tracking device (hereinafter "accuracy device") may include a rigid object such as, for example, a block of material. The rigid object may comprise a material (e.g., plastic or other material) that is known not to cause distortions in a field (e.g., magnetic field or other field) utilized by the tracking device whose accuracy is to be ensured. In some embodiments, the rigid object may be manufactured as a latticework. Other constructions and/or types of rigid objects may be used.

The rigid object may be equipped with one or more position indicating elements embedded in or located on the rigid object. In one embodiment, the position indicating elements may include magnetic sensor coils that may be part of a magnetic tracking device. In one embodiment, the position indicating elements may be placed at known points or locations in or on the rigid object.

The rigid object and the position indicating elements may be constructed such that the position, orientation, or other information regarding the position indicating elements or the known points corresponding to the position indicating elements are determinable to a high degree of accuracy either by post-manufacture measurement or precise manufacturing specifications and techniques. This position and/or orientation data may be referred to as "baseline data" or the "true positions" of the position indicating elements or corresponding known points.

In one embodiment, the rigid object may be associated with its own frame of reference or coordinate system. The a priori or baseline data regarding the position indicating elements or their corresponding known points may be expressed relative to the frame of reference of the rigid object. As discussed below, because each of the position indicating elements or known points may also be associated with its own frame of reference/coordinate system, the baseline data regarding the position indicating elements or corresponding known points may also be expressed relative to one another.

In one embodiment, the accuracy device may include a tracking device. The tracking device may comprise a field generator, a control unit, and/or other elements. In some embodiments, the tracking device may comprise, for example, a magnetic tracking device, in which case the field generator may comprise a magnetic field generator and the position indicating elements may comprise magnetic position sensors.

In some embodiments, the tracking device may include, or be operatively connected to, a computer or a computer system. In some embodiments, the computer system may collect, store, transmit, manipulate, and/or analyze data regarding the tracking device, the position indicating elements, a priori data regarding the rigid object, and/or other data involved in ensuring the accuracy of a tracking device or performing other functions of the invention described herein. In some embodiments, data regarding the tracking device, any position indicating elements associated therewith, their corresponding known points, or other data may be stored in a memory device such as, for example a read-only memory (ROM), incorporated into the tracking device and readable by the computer system.

The position indicating elements may be sampled by the tracking device to provide position and/or orientation information regarding the position indicating elements. This sampled position and/or orientation information regarding each of the position indicating elements may be expressed relative to one another or in the frame of reference of the tracking device. This sampled position, orientation, and/or other information may be compared to the aforementioned baseline data for the purposes of detecting errors in the tracking device, "zeroing" the tracking device, detecting distortions in a surgical or other experimental environment, correcting or re-calibrating the tracking device to account for any such distortions, and/or for other purposes.

In one embodiment, the invention provides a process for testing and correcting the accuracy of a tracking device using the accuracy device. Initially, baseline position and/or orientation data regarding one or more position indicating elements or corresponding points/locations within the rigid object of the accuracy device (e.g., "baseline data") may be obtained. In one embodiment, the accuracy device may then be placed in an environment that is known to be free of disturbing influences (e.g., an "undistorted volume") and position and/or orientation information regarding the position indicating elements of the rigid object may be sampled.

In one embodiment, the baseline data may then be compared to the sampled data from the undistorted volume. If the difference between the baseline data and the sampled data is greater than a predetermined threshold, the tracking device may be considered out of calibration. If the difference between the baseline data and the sampled data is less than or equal to the predetermined threshold, the rigid object may then be placed in an experimental volume. As used herein, an "experimental volume" may include an unknown volume or environment that may include distortions such as, for example, a surgical environment or other investigative environment. Position and/or orientation information regarding the position indicating elements in the experimental volume may then be sampled in the experimental volume.

In one embodiment, the sampled data from the undistorted volume may be compared with the sampled data from the experimental volume and the baseline data may be compared to the sampled data from the experimental volume. If either comparison yields a difference that is greater than a predetermined threshold, the tracking device may be considered out of calibration. If both of the comparisons yield differences that are not greater than the predetermined threshold, then surgery or other procedures may be conducted in the experimental volume.

If the tracking device is considered out of calibration, an error function may be calculated over the volume of the rigid object. In some embodiments, samples of the distortion may be taken multiple times and/or in multiple places within the experimental volume to generate an error function that better characterizes the experimental volume. The resultant error function may then be used to create a "correction map" that is applied to the tracking device to correct for the distortions in the experimental volume.

Once the tracking device has been corrected for any distortions, the tracking device may be used to track position indicating elements for various purposes such as, for example: registration of multiple sets of data for image guided surgery; verification of such registration; dynamic referencing of a portion of a surgical patient for image guided surgery; gating of image, position, electrical, or other data prior to or during surgery; tracking instruments during image guided surgery; or for other purposes.

In some embodiments, the aforementioned computer system may include one or more computers and one or more modules (e.g., software modules, firmware modules, or other modules) for performing various functions for ensuring the accuracy of a tracking device according to the invention. These various functions may include, for example, comparing baseline data to sampled position and/or orientation information (undistorted or experimental) of one or more of the position indicating elements, calculating an error function or a correction map characterizing any distortions in a volume or environment (e.g., a distorted experimental environment), applying the correction map to the tracking device, registering sampled position and/or orientation information to a frame of reference of the rigid object, registering any set of data from one frame of reference to the frame of reference of another, or for performing other features or functions described herein. In some embodiments, some or all of the features or functions may be performed by hand or otherwise performed without the use of a computer or computer system.

The various objects, features, and advantages of the invention will be apparent through the detailed description of the preferred embodiments and the drawings attached hereto. It is also to be understood that the following detailed description is exemplary and not restrictive of the scope of the invention.

DETAILED DESCRIPTION OF PREFERRED EMBODIMENTS

The invention provides systems and methods for ensuring the accuracy of a tracking device that provides position and orientation information of one or more position indicating elements in a volume. The system for ensuring the accuracy of a tracking device (hereinafter "accuracy device") and the methods for use thereof according to the invention ensure the accuracy of a tracking device by detecting distortions in and correcting, according to those distortions, the magnetic or other field generated by a field generator associated with the tracking device.

Figure 1:
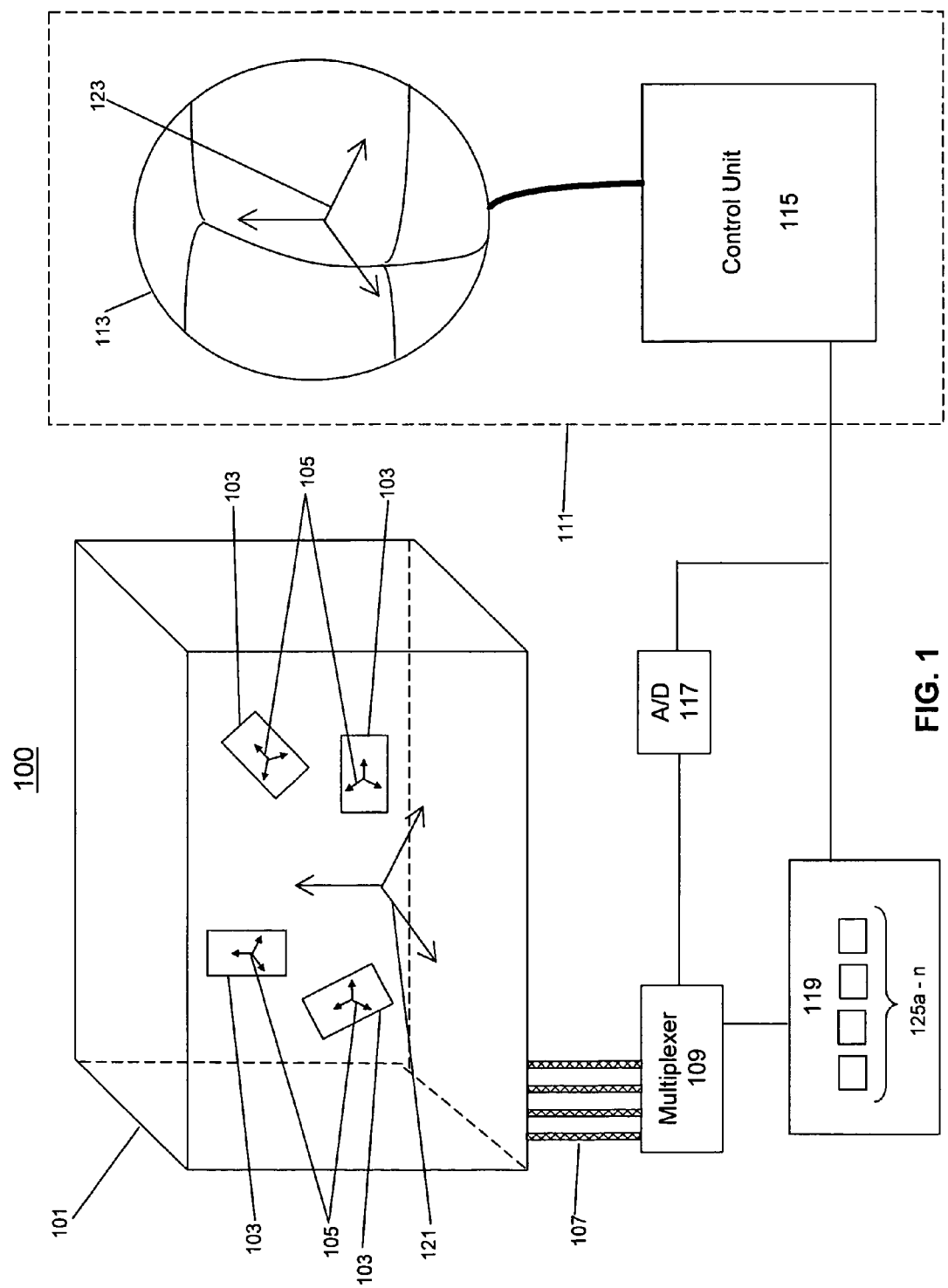
FIG. 1 illustrates an accuracy device according to one embodiment of the invention.

FIG. 1 illustrates an accuracy device 100 according to one embodiment of the invention. In one embodiment, accuracy device 100 may include a rigid object such as, for example, block of material 101. Block 101 may comprise a material (e.g., plastic or other material) that is known not to cause distortions in the magnetic field or other field utilized by the tracking device whose accuracy is to be ensured. In some embodiments, block 101 may be a solid or substantially solid block. In some embodiments, block 101 may include any shaped volume of material. In some embodiments, block 101 may be manufactured as a latticework. Block 101 or other rigid objects may be fabricated using conventional manual or numerical machining techniques or, in some embodiments, using common rapid prototyping techniques such as, for example, stereolithography (SLA), fused deposition modeling (FDM), selective laser sintering (SLS), 3D printing, or other techniques. Other constructions for block 101 may be used and/or other types of rigid objects may be used.

Block 101 may be equipped with a plurality of position indicating elements 103. In one embodiment, position indicating elements 103 may be embedded in to block 101. In one embodiment, position indicating elements 103 may include magnetic sensor coils that may be part of a magnetic tracking device. In one embodiment, position indicating elements 103 may be placed at known points in or on block 101. In one embodiment, block 101 may comprise a material that is radiolucent such as, for example, non-conductive plastic, so that the locations of embedded objects can be verified by an imaging modality (for example X-ray).

In some embodiments, a local coordinate system 105 may be associated with each position indicating element 103 or its corresponding known point. The number, position and orientation of position indicating element 103 may vary to the extent that position indicating elements 103 be placed in sufficiently different locations such that they do not interfere with one another, and provide a plurality of locations and orientations. For example, in an embodiment utilizing magnetic position sensors as position indicating elements, sensors placed immediately adjacent to one another may cause local distortions. Thus, in some embodiments, care should be taken to provide sufficient spacing between position indicating elements.

Block 101 with position indicating elements 103 may be constructed such that the position and orientation information regarding position indicating elements 103 or other corresponding known points within block 101 are determinable to a high degree of accuracy either by post-manufacture measurement or precise manufacturing specifications and techniques. This position and/or orientation data may be referred to as "baseline data" or the "true positions" of position indicating elements 103. As mentioned above, the positions and/or orientation of the position indicating elements 103 within block 101 may intentionally correspond to known points or locations within or upon block 101.

In one embodiment, block 101 may be associated with its own frame of reference or coordinate system 121. The a priori or baseline data regarding the known points/locations or position and orientation information of position indicating elements 103 may be known relative to coordinate system 121. As discussed below, because each of position indicating elements 103 may also be associated with its own frame of reference or coordinate system 105, the known points/locations or position and orientation information of position indicating elements 103 may also be known relative to one another.

In one embodiment, accuracy device 100 may include a tracking device 111. Tracking device 111 may comprise a field generator 113 and a control unit 115. In some embodiments, tracking device 111 may comprise, for example, a magnetic tracking device, in which case field generator 113 may comprise a magnetic field generator and position indicating elements 103 may comprise magnetic position sensors.

In one embodiment, a wiring element 107 may be associated with each position indicating element 103. In one embodiment, wiring element 107 may comprise, for example, a shielded twisted pair cable. In some embodiments, wiring element 107 may connect each position indicating element 103 to tracking device 111. In some embodiments, a multiplexer 109 may exist between wiring elements 107 and tracking device 111. In some embodiments, multiplexer 109 may enable the sampling of information from multiple position indicating elements 103 via a single channel of tracking device 111 by cycling through each of position indicating elements 103 in response to a control signal from tracking device 111 or a computer system 119 connected to tracking device 111. In one embodiment, multiplexer 109 may comprise a bank of relay switches or other suitable switching elements that are controlled by suitable logic elements. Each time a control signal is generated by tracking device 111 or computer system 119, the logic elements in the multiplexer cause a relay to connect a different position indicating element 103 to tracking device 111.

In some embodiments, an analog/digital (A/D) converter 117 may exist between wiring elements 107 and tracking device 111. A/D converter 117 may serve to convert analog signals from position indicating elements 103 into digital signals that may be processed by tracking device 111 and/or computer system 119. While FIG. 1 illustrates A/D converter 117 between multiplexer 109 and tracking device 111, A/D converter 117 may also be placed between multiplexer 109 and position indicating elements 103 in some implementations. In some embodiments, neither multiplexer 109, nor A/D converter 117 may be used.

In some embodiments, tracking device 111 may include, or be operatively connected to, computer system 119. As mentioned above, computer system 119 may directly control multiplexer 109 using control signals. In some embodiments, computer system 119 may collect, store, transmit, manipulate, and/or analyze data regarding tracking device 111, position indicating elements 103, a priori data regarding a rigid object such as block 101, and/or other data involved in ensuring the accuracy of tracking device 111 or for performing other features or functions of the invention described herein. In some embodiments, data regarding tracking device 111, any position indicating elements 103 associated therewith, their corresponding known points, or other data may be stored in a memory device incorporated into tracking device 111 and readable by computer system 119.

Position indicating elements 103 may be sampled by tracking device 111 and may provide position, and/or orientation, information regarding position indicating elements 103 to tracking device 111 in a frame of reference or coordinate system 123 of tracking device 111. Also, because there may be multiple position indicating elements 103, each of which are associated with a coordinate system 105, position and/or orientation information regarding each of position indicating elements 103 may be expressed relative to one another. As discussed below, this sampled position, orientation, and/or other information may be utilized for comparison to the aforementioned baseline data for the purposes of calibration of tracking device 111, detection of distortions in a surgical or other experimental environment, correction or re-calibration of tracking device to account for such distortions, and/or for other purposes.

Figure 2A:
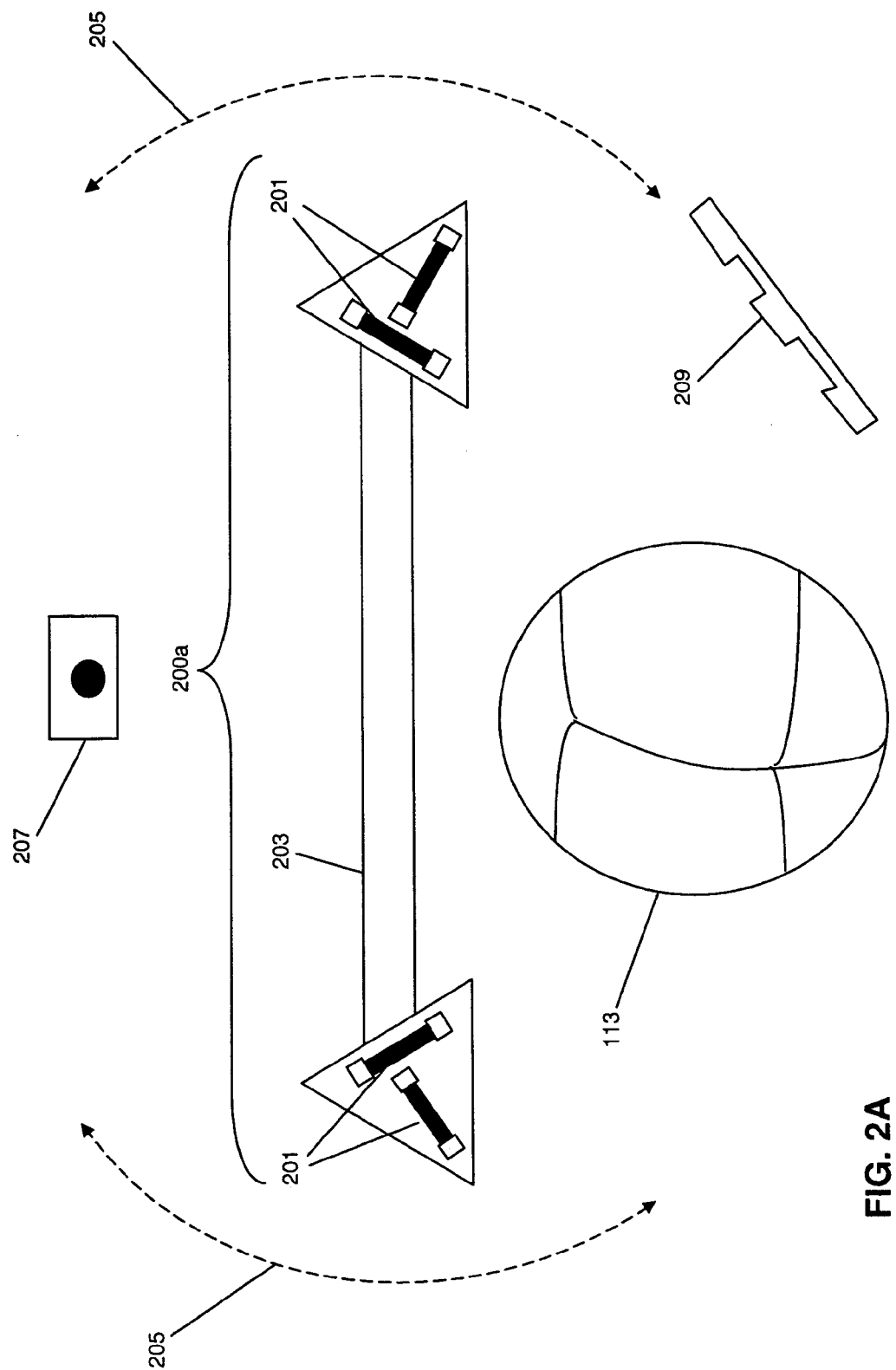
FIG. 2A illustrates a rigid object according to an embodiment of the invention.
Figure 2B:
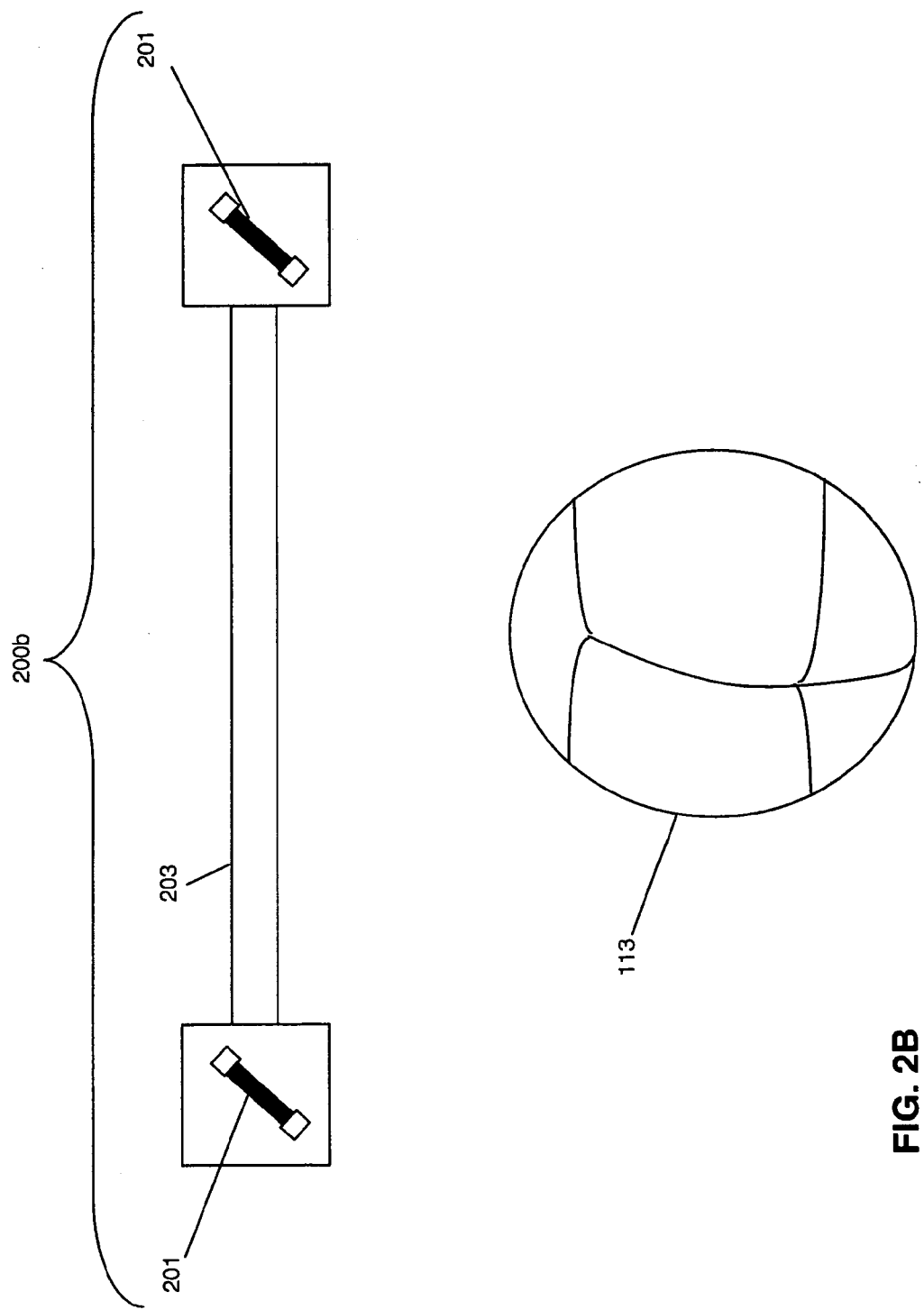
FIG. 2B illustrates a rigid object according to an embodiment of the invention.

FIGS. 2A and 2B illustrate offset objects 200a and 200b of accuracy device 100 according to another embodiment of the invention. In some embodiments, the rigid object of accuracy device 100 may comprise an offset object (e.g., offset objects 200a or 200b). An offset object may include position indicating elements 201 separated by an offset such as a bar 203. FIG. 2A illustrates offset object 200a with 2 groups of 2 position indicating elements 201 (four position indicating elements 201 in total). FIG. 2B illustrates an embodiment wherein offset object 200b has two individual position indicating elements 201. In some embodiments, offset objects 200a and/or 200b may be used as a rigid object place of or in addition to block 101.

Referring back to FIG. 1, as described below, tracking device 111 may sample position and/or orientation information regarding one or more position indicating elements 103 for use in calibrating and/or ensuring the accuracy of tracking device 111 or for other purposes. In one embodiment, the rigid object such as, for example, block 101 may be placed into a volume or environment. The volume should exist within the field of tracking device 111. The position and/or orientation of position indicating elements 103 may then be sampled by tracking device 111.

In one embodiment, block 101 may be placed, and the position and/or orientation of position indicating elements 103 sampled, in several positions relative to field generator 113. If sampling is performed quickly enough, sampling position and/or orientation information of position indicating elements 103 may be done as a continual recording as block 101 is moved within the volume. In this embodiment, the position and/or orientation information of position indicating elements 103 may be sampled at different instants in time, each element moving to a slightly different position for each sample.

In another embodiment, position indicating elements 103 may be sampled in a series of discrete, quasi-static movements, for example:

1) block 101 may be positioned in a location in the field of tracking device 111;
2) block 101 may then be temporarily fixed in that location;
3) position and/or orientation information of position indicating elements 103 may then be sampled by tracking device 111;
4) block 101 may then be moved to a second location and the position and/or orientation information of position indicating elements 103 may be sampled again;
5) this movement-sampling procedure may be performed multiple times.

The position/orientation information of position indicating elements 103 relative to one another in each of the sampling locations may then be compared to obtain "relative sensor comparison" information. This relative sensor comparison may be used in the processes described in detail below to express position information data in an undistorted and/or experimental volume for calibration, characterization, correction, or other purposes.

Figure 3A:
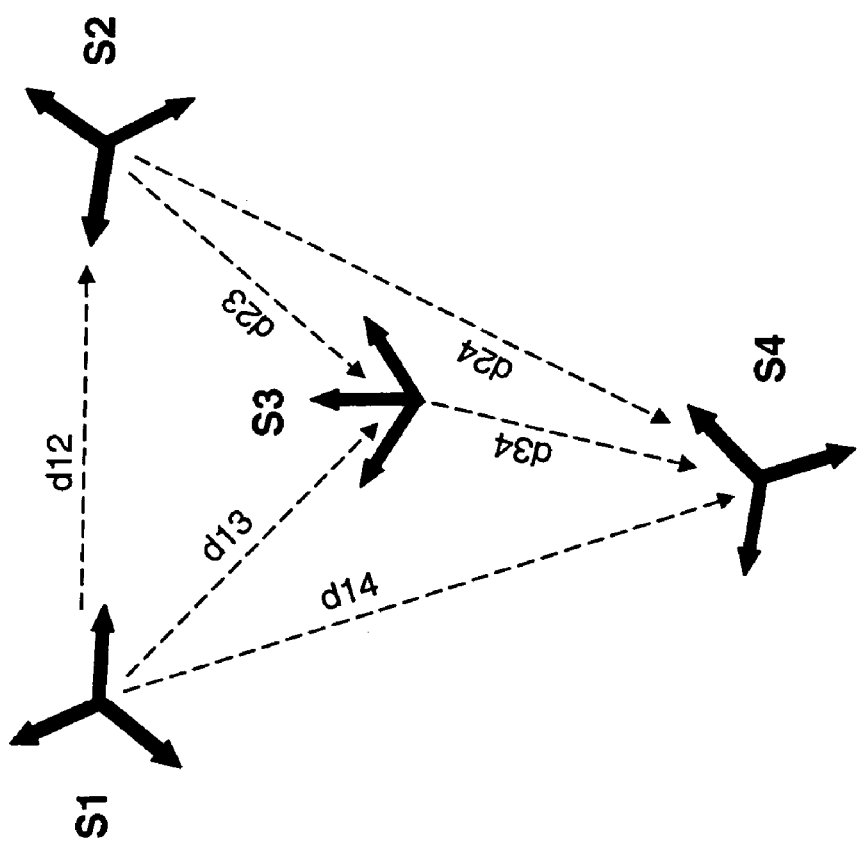
FIG. 3A illustrates relative positions of position indicating elements and distances between them according to an embodiment of the invention.

In some embodiments, relative sensor comparison may take the form of a distance computation between all combinations of position indicating element pairs in block 101 and a dot or cross product calculation between all combinations of position indicating element pairs in block 101 to compare angles. As an example, these distances are indicated in FIG. 3A as $d_{12}$, $d_{13}$, $d_{14}$, $d_{23}$, $d_{24}$, $d_{34}$. The cross products $d_{12} \times d_{13}$, $d_{13} \times d_{14}$, etc., for example, could be formed.

In one embodiment, it is also possible to determine position/orientation information of position indicating elements 103 relative to a single suitable fixed coordinate system ("fixed frame comparison") such as, for example, fame of reference/coordinate system 121 associated with block 101, as illustrated in FIG. 1.

Figure 3B:
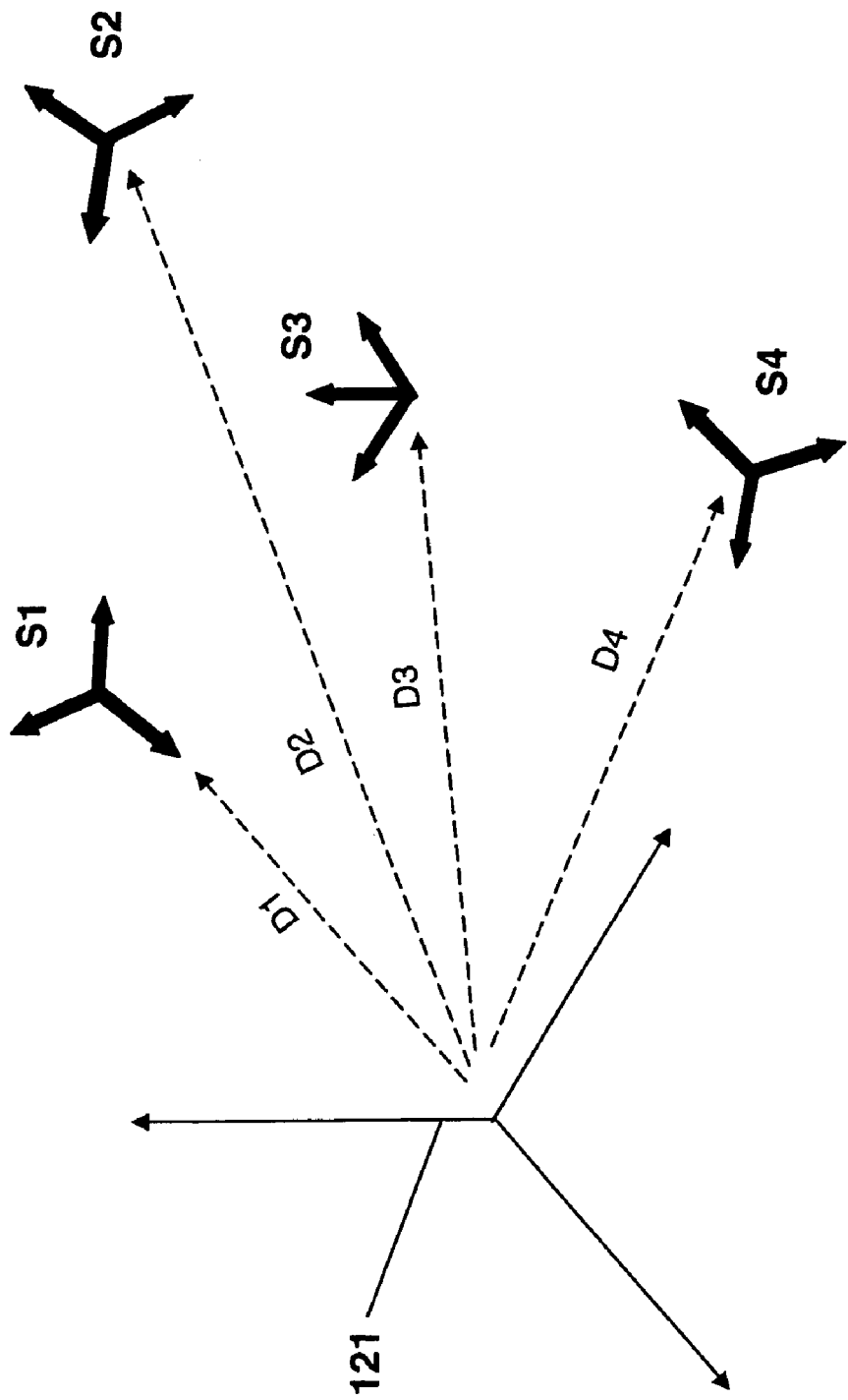
FIG. 3B illustrates positions of position indicating elements relative to a common frame of reference according to an embodiment of the invention.

In one embodiment, a fixed frame comparison might take the form of a distance computation between all position indicating elements and fixed coordinate system 121. FIG. 3B illustrates these distances as $D_1$, $D_2$, $D_3$, $D_4$.

In both relative sensor comparison and fixed frame comparison, the data obtained by sampling using tracking device 111 may be compared to the a priori data regarding location and/or orientation of the known points of the rigid object or position indicating elements 103 (e.g., the baseline data) as previously measured or established. If the sampled information is taken from a known undistorted volume, this comparison enables a user to determine if field generator 113 and/or tracking device 111 is operating properly, as deviations between the baseline data and sampled data would indicate an error due in tracking device 111 itself. If the sampled information is taken from an experimental volume, this comparison enables characterization of the experimental volume, including any distortions therein, correction of such distortions, and/or other features of the invention.

Comparison of the a priori baseline position and/or orientation information to the sampled position and/or orientation information from a controlled, undistorted environment may be known as a "baseline comparison." When performing baseline comparisons, care may be taken to ensure that the temperature and other circumstances of the block are the same as during collection of baseline data (e.g., during initial measurement or manufacturing of the rigid object).

As mentioned above, comparison of the a priori baseline data to experimental position and/or orientation data enables characterization of a distorted experimental volume and calibration of a tracking device to correct for such distortions. Characterization alone may increase the accuracy of sampling within both distorted and undistorted volumes/environments. Characterization and correction of distortions involves the use of a correction functions such as, for example, smoothing functions or a "lookup table" (LUT) of correction parameters and terms that can be applied in the experimental volume and that are individually tailored for the specific distortions in the specific experimental volume at hand.

In one embodiment, characterization of an experimental volume (e.g., a distorted surgical environment) may include sampling and recording position and/or orientation information of position indicating elements 103 (or 201). This data serves as the basis for forming the correction. Comparison of this distorted surgical environment data to baseline data acquired from manufacturing/measurement and/or sampled data obtained in a known, undistorted environment provides the necessary information for performing the correction.

This characterization and comparison may enable a "correction map" to be obtained for the distorted experimental volume, which may be applied to tracking device 111 to correct for the distortions. This enables more accurate readings from tracking device 111. Mathematical methods of correction of error between the baseline data (e.g., "true positions"), undistorted volume data (e.g., "measured positions") and distorted experimental volume data (e.g., the "surgical positions") using different space characterization techniques are known in the art. These methods may be adopted to perform the required calculations for use of the invention. See e.g., X. Wu and R. Taylor, *Medical Image Computing and Computer-Assisted Intervention*, MICCAI 2003; Lecture Notes in Computer Science, Vol. 2879 (2003), (Randy E. Ellis, Terry M. Peters eds.; Springer-Verlag Heidelberg Publishers), pp. 215-222. The overall result of the characterization is to obtain a correction map of the experimental volume that is then applied to tracking device 111 to increase the accuracy of measurement in that volume. Tracking device 111 may then be used to track position indicating elements (103, 201, or others) for various purposes such as, for example: registration of multiple data sets for image guided surgery; verification of such registration; dynamic referencing of a portion of a surgical patient for image-guided surgery; gating of image, position, electrical, or other data for tracking instruments during image guided surgery; for performing image-guided surgery; or for other purposes.

When comparing position/orientation data using "relative sensor comparison," it may not be necessary to co-align or "register" the position and orientation of coordinate systems 105 of position indicating elements 103 with coordinate system 121 of block 111. Here, the inter-sensor orientations and distances are being compared to the baseline data, each of which exist in local coordinate system 105 of individual position indicating elements 103. These inter-sensor orientations and distance values are independent with the orientation of block 111 relative to field generator 113's coordinate system 123.

If however, fixed frame comparison is used, the frame of reference of the a priori baseline data is coordinate system 121 of block 101. The frame of reference of the sampled data is coordinate system 123 of the tracking device. As such, in order to compare the two sets of data, a registration process must be undertaken to transform the sampled data measured in coordinate system 123 to the fixed coordinate frame 121 of block 101 or vice versa. This may be done by several methods, such as:

a) a method known in the art such as, for example, singular valued decomposition or the iterative closest points technique. These techniques may be used to perform the necessary registration based on the position of some, or all of the position indicating elements 103. A priori baseline position and/or orientation information in block 101's coordinate system 121 may be matched to the coordinates of position indicating elements 103 measured in coordinate system 123 of tracking device 111;

b) divot locations on block 101 may be sampled using a tracked probe and may also be employed to perform the necessary registration to coordinate system 121 if the divot locations are known in coordinate system 121 and in coordinate system 123;

c) block 101 may also be placed in a fixed relationship to field generator 113 using an alignment apparatus so that the relationship between coordinate systems 121 and 123 is known beforehand; or d) other registration techniques may be used.

It may be noted that the process of registration itself may be used to supply an averaged value of any distortion due to the environment or inaccuracy of the position sensor by calculating a root mean square (RMS) based on position indicating elements 103 that are used for registration. In this process, the average registration transformation may be first calculated, and each known position indicating element location is transformed according to the average transformation. The difference between the baseline location of each position indicating element and the sampled locations of each position indicating element may be reported as the RMS. An RMS of 0 indicates perfect registration. The RMS is an indication of the current accuracy of the tracking device. This method is often used in image guided surgery to evaluate the quality of a registration, but in this situation can also provide a method of evaluating the amount of distortion.

Initial data gathering in a controlled/unperturbed environment and baseline comparison may be used to "zero" accuracy device 100 so that an indication of the baseline accuracy of tracking device 111 is available, irrespective of the measured accuracy of tracking device 111 at the time of that measurement. Here, the baseline accuracy of tracking device 111 may not used except to be recorded as the current status of the system. The position and/or orientation information sampled in the known undistorted volume may then be used to compare any subsequent sampled information in an unknown/experimental volume for distortions.

Figure 4A:
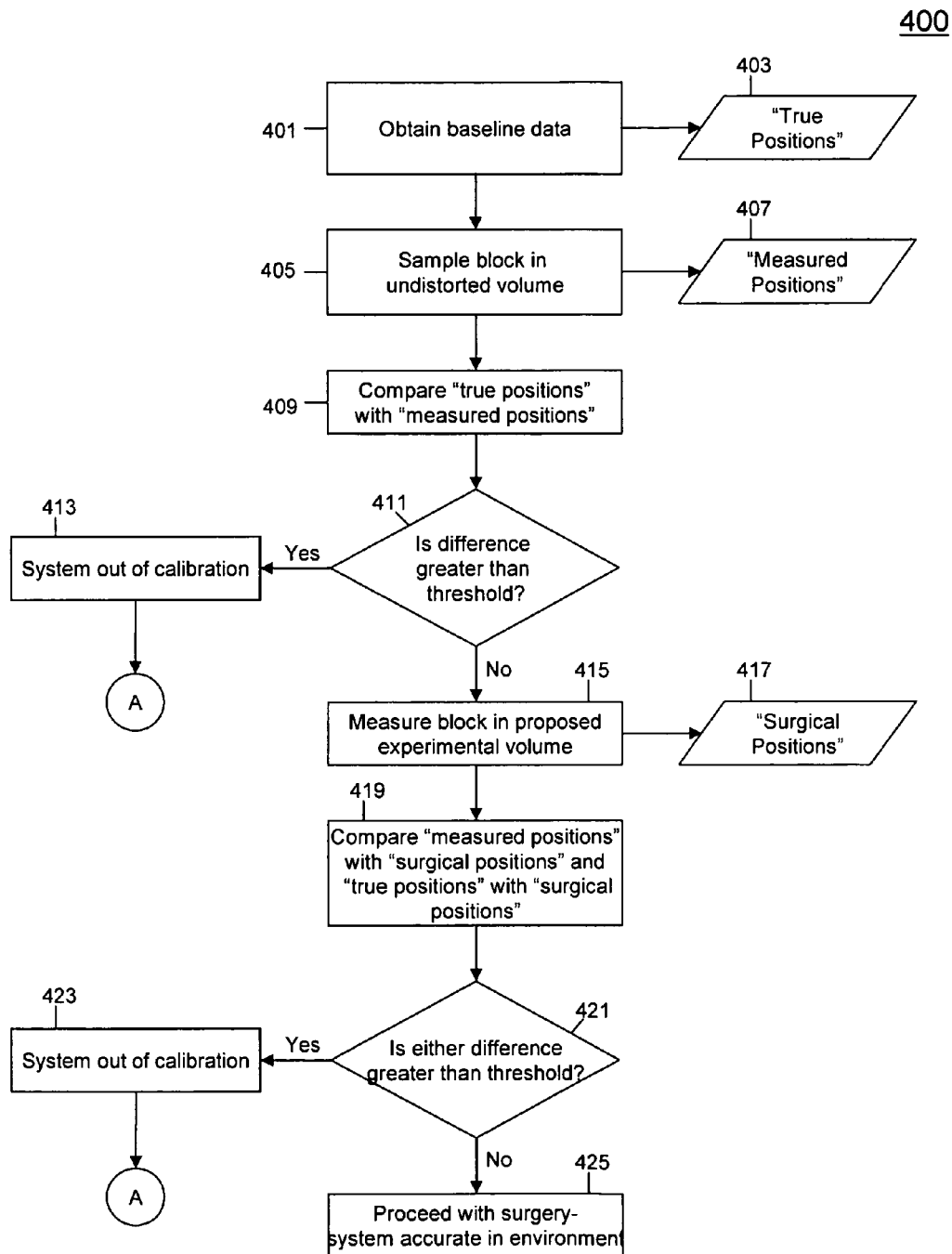
FIG. 4A illustrates a process according to an embodiment of the invention.
Figure 4B:
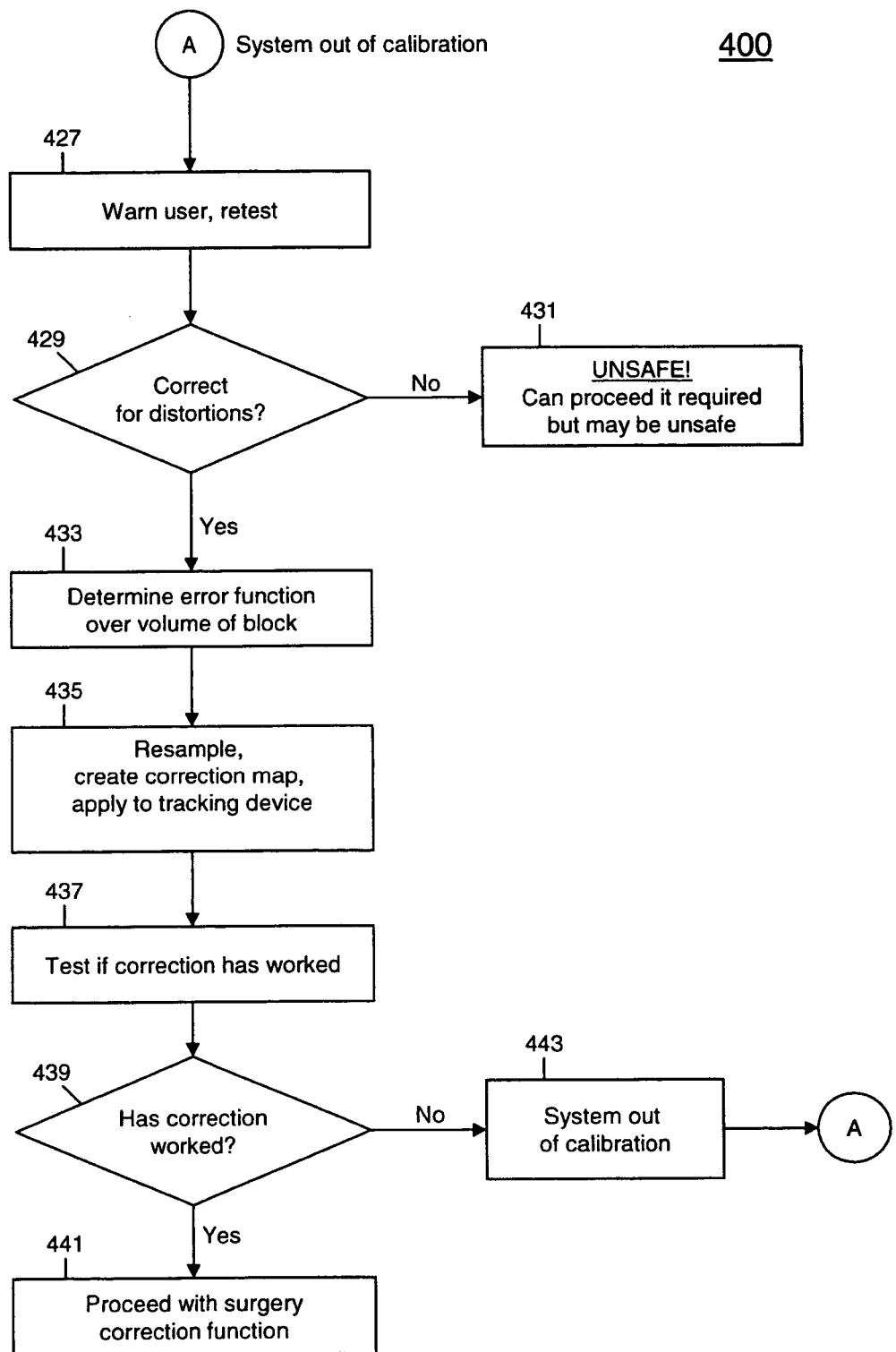
FIG. 4B illustrates a process according to an embodiment of the invention.

FIGS. 4A and 4B illustrate a process 400 according to an embodiment of the invention, wherein the accuracy of tracking device 111 may be tested and corrected for distortions in an experimental volume using accuracy device 100. As used herein, an "experimental volume" may include an unknown volume or environment such as, for example, a surgical environment or other investigative environment. FIG. 4A illustrates a portion of process 400 including an operation 401, wherein baseline position and/or orientation data may be obtained. The resultant data may be considered the "true positions" of position indicating elements 103, as indicated by a data item 403.

In an operation 405, accuracy device 100 may be placed in an environment that is known to be free of disturbing influences (an "undistorted volume") and position and/or orientation information regarding position indicating elements 103 may be sampled. This data may be indicated as the "measured positions" of position indicating elements 103 in the undistorted volume, as indicated by a data item 407.

In an operation 411, the true positions of data item 403 may be compared to the measured positions of data item 407. As discussed above, this may indicate any errors existing within tracking system 111, may serve to "zero" tracking system 111, or may be used for other purposes. If, in an operation 411, the difference between the true positions and the measured positions is greater than a predetermined threshold, tracking device 111 is considered out of calibration as indicated by an operation 413.

If, in operation 411, the difference between the true positions and the measured positions is less than or equal to the predetermined threshold, process 400 may proceed to an operation 415. In an operation 415, the block may be placed in an experimental volume such as, for example, a surgical or other investigative environment, and position and/or orientation information regarding position indicating elements 103 may be sampled. This data may be designated the "surgical positions" of position indicating elements 103, as indicated by a data item 417.

In an operation 419 the measured positions of data item 407 may be compared with the surgical positions of data item 417 and the true positions of data item 403 may be compared to the surgical positions of data item 417. If, in an operation 421, either the difference between the measured positions and the surgical positions or the difference between the true positions and the surgical positions are greater than predetermined thresholds (the values of which may be the same or different from other thresholds used in the processes of the invention) process 400 proceeds to an operation 423, wherein tracking device 111 is considered out of calibration in the experimental volume. If, in an operation 421, both the difference between the measured positions and the surgical positions and the difference between the true positions and the surgical positions is equal to or less than predetermined thresholds, then process 400 proceeds to an operation 425, wherein surgery may be conducted in the current surgical environment.

FIG. 4B illustrates a part of process 400 wherein tracking device 111 is considered out of calibration. In an operation 427, tracking device 111 is considered out of calibration, and the user may be warned of such and one or more of operations 401 through 425 may be performed to re-test the accuracy of tracking device 111. If, in an operation 429, the user decides not to correct tracking device 111 for distortions, process 400 may proceed to an operation 431, wherein tracking device 111 may be considered unsafe but usable, if use is necessary and the user determines that for the particular use the accuracy is sufficient.

If, in operation 429, the user and/or accuracy device 100 decides to correct tracking device 111 for distortions, process 400 may proceed to an operation 433, wherein an error function over the volume of block 101 may be calculated. In an operation 435, samples of the distortion may be taken multiple times, and/or from multiple places within the experimental volume to generate an error function that better characterizes the experimental volume. This error function may be used to create a lookup table (LUT), smooth correction functions (based on multiple parameters determined from measurements), and/or other distortion correction correlation representing the distortions (hereinafter referred to as a "correction map"). Also in operation 435, the correction map may be applied to tracking device 111 to correct for the distortions in the experimental volume. In an operation 437, tracking device 111 may be re-tested in the experimental volume (e.g., new "surgical positions" sampled and compared to the "true positions" and/or "measured positions") to see if the corrections have work sufficiently. If, in an operation 439, it is determined that the correction has worked, process 400 may proceed to an operation 441, wherein surgery may proceed. If, in operation 439, it is determined that the corrections have not worked sufficiently, process 400 may proceed to an operation 443, wherein tracking device may be considered out of calibration.

In one embodiment (not illustrated), block 101 may be equipped with a plurality of holes, each of which can house a position indicating element 103. Alternatively, a position indicating element 103 may be attached to a probe or wand which is sequentially inserted into each hole and sampled by tracking device 111 to obtain position and/or orientation information.

In still another embodiment, block 101 may include a tortuous pathway or conduit that can be navigated using a wire, tube, cannula, or other device containing one or more position indicating elements 103 in a manner described by U.S. patent application Ser. No. 11/059,336, entitled "Method and Apparatus for Registration, Verification, and Referencing of Internal Organs," which is hereby incorporated by reference herein in its entirety. The pathway coordinates may be known a priori (e.g., baseline data) and position indicating elements 103 may be guided through the path while its position, orientation and/or other information is continuously sampled by tracking device 111. Once the entire path is traversed with the wire, the coordinates and slopes may be compared to the known coordinates and slopes of the pathway.

Figure 5:
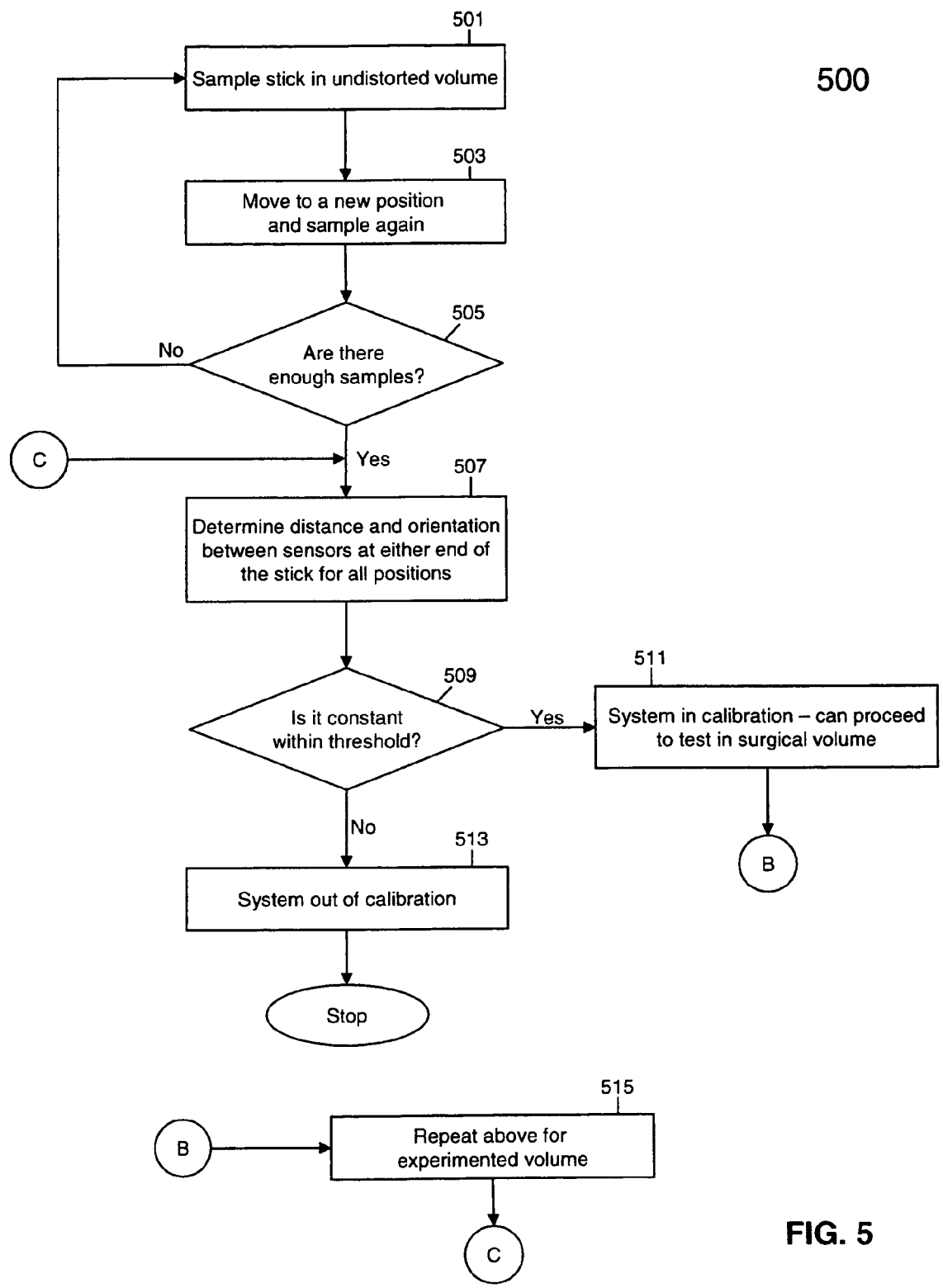
FIG. 5 illustrates a process according to an embodiment of the invention.

FIG. 5 illustrates a process 500 according to an embodiment of the invention, wherein the accuracy of tracking device 111 may be tested using an offset device (e.g., offset device 200a or 200b of FIG. 2A or 2B) as the rigid object of accuracy device 100. The use of the offset device may potentially avoid the need to use multiplexer 109, enabling multiple samples to be obtained quickly and rapidly by sampling the space. When using the offset device rather than block 101, it may not be as easy to re-characterize the space in which the device resides unless the offset device is tracked using a device other than tracking device 111 such as, for example a camera system 207 and/or an optical tracker, 209. However, the use of the offset device is simpler in construction and less obtrusive than block 101.

In an operation 501, position, orientation or other information regarding position indicating elements 201 of the offset device may be sampled in a known, undistorted volume by tracking device 111. In an operation 503, the offset device may be moved to a new position and/or orientation within the undistorted volume and position and/or orientation information may again be sampled by tracking device 111. In some embodiments, the position, orientation or other information may be obtained as the offset device is moved dynamically in the experimental volume and the position and/or orientation information is sampled during the dynamic or quasi-static movement.

If, in an operation 505 it is decided that there is not enough position and/or orientation information, process 500 may return to operation 501. If, in an operation 505 it is decided that there is enough position and/or orientation information, process 500 may proceed to operation 507, wherein the distance and orientation information between all position indicating elements 201 at opposing ends of the offset device may be determined for all sampled positions of the offset device.

If, in an operation 509, it is determined that the distance and orientation between position indicating elements 201 at opposing ends of the offset device is constant within a predetermined threshold for all positions sampled, process 500 may proceed to an operation 511 wherein the tracking system is considered in calibration and an experimental volume may be tested in the same manner as above (e.g., similar to operations 501 through 509, except in experimental volume) in an operation 515. If however, in an operation 509, it is determined that the distance and orientation between position indicating elements 201 at opposing ends of the offset device is not constant within a predetermined threshold for all positions sampled, process 500 may proceed to an operation 513, wherein the system may be considered out of calibration and corrective measures may be taken. Such corrective measures may include determining distortion functions over the experimental volume, creating a correction map, applying the correction map to tracking device 111, testing the correction, or other operations.

In some embodiments, block 101 may be used as a multi-function device that can be used, for example, to provide a dynamic referencing device when it is not in use as a part of an accuracy device 100. Additionally, block 101 may also be used to assist in calibrating and registering fluoroscopic images.

Referring back to FIG. 1, computer system 119 may include one or more computers (e.g., servers, PCs, laptops, or other computers) and one or more software modules 125a-n for performing various functions for ensuring the accuracy of tracking device 111 according to the invention. For example, computer system 119 may include a comparison module for comparing baseline data to position/orientation information (e.g., undistorted or experimental position/orientation information) of one or more position indicating elements 103 or 201 or for performing other comparisons. Computer system 119 may also include a correction map module for calculating one or more error functions, look up tables, and/or correction maps for characterizing a volume and any distortions therein. Computer system 119 may also include a correction module for applying a correction map or correction function to tracking device 111 to correct for any distortions in a volume. Computer system 119 may also include a registration module for registering position and/or orientation information from one frame of reference to another or for registering any number of data sets from multiple frames of reference to a single frame of reference. Computer system 119 may also include other modules for performing other features or functions of the invention. In some embodiments, some of these tasks may be performed on or transferred to control unit 115.

Those having skill in the art will appreciate that the invention described herein may work with various system configurations. It should also be understood that various software modules 125a-n that are utilized to accomplish the functionalities described herein may be maintained on computer system 119, control unit 115 or other components of accuracy device 100, as necessary. In other embodiments, as would be appreciated, the functionalities described herein may be implemented in various combinations of hardware and/or firmware, in addition to, or instead of, software.

Other embodiments, uses and advantages of the invention will be apparent to those skilled in the art from consideration of the specification and practice of the invention disclosed herein. The specification should be considered exemplary only, and the scope of the invention is accordingly intended to be limited only by the following claims.

I claim:

1. A method for detecting and correcting an existence of one or more distortions in an electromagnetic field created using a magnetic tracking device for image guided surgery, wherein the one or more distortions originate from a volume of space where a medical procedure is to be performed using the magnetic tracking device and decrease an accuracy of the magnetic tracking device, the method comprising:

placing, prior to performing the medical procedure, a rigid object into the volume of space, wherein the rigid object comprises one or more position indicating elements at one or more known locations of the rigid object, and wherein the one or more position indicating elements are associated with baseline position and orientation information that indicates known position and orientation of the one or more known locations prior to first use of the rigid object;

obtaining sampled position and orientation information of the one or more position indicating elements in the volume of space;

comparing the sampled position and orientation information to the baseline position and orientation information of the one or more position indicating elements; and determining the existence of the one or more distortions in the electromagnetic field that originated from the volume of space and that are imposed upon the one or more known locations based on the comparison, whereby the decrease in the accuracy of the magnetic tracking device resulting from the one or more distortions is at least partially correctable based on the determination when the medical procedure using the magnetic tracking device is performed.

2. The method of claim 1, the method further comprising:

characterizing the one or more distortions in the volume of space when a difference between the sampled position and orientation information and the baseline position and orientation information exceeds a predetermined threshold;

creating a correction map, based on the characterizing, that enables adjustment of the magnetic tracking device to correct for the one or more distortions in the volume of space; and adjusting the magnetic tracking device according to the correction map.

3. The method of claim 2, further comprising:

conducting the medical procedure in the volume of space while the rigid object is in the volume of space; and monitoring, while the medical procedure is being conducted, the volume of space for distortions by periodically obtaining additional sampled position and orientation information and comparing the additional sampled position and orientation information to the baseline position and orientation information.

4. The method of claim 2, further comprising:

conducting the medical procedure in the volume of space while the rigid object is in the volume of space; and dynamically referencing at least a portion of a subject of the medical procedure using the one or more position indicating elements.

5. The method of claim 4, wherein a dynamic reference for use during said dynamically referencing is the rigid object.

6. The method of claim 1, further comprising registering the sampled position and orientation information to a frame of reference of the rigid object.

7. The method of claim 1, wherein each of the one or more position indicating elements are connected to a multiplexer, and wherein the sampled position and orientation information is obtained by the magnetic tracking device via cycling through the one or more position indicating elements using the multiplexer.

8. The method of claim 1, wherein the rigid object comprises one or more predefined passageways within the rigid object, the method further comprising:

positioning the magnetic tracking device within the one or more predefined passageways;

causing the magnetic tracking device to traverse the one or more predefined passageways, wherein said obtaining sampled position and orientation information further comprises obtaining sampled position and orientation information as magnetic tracking device traverses the one or more predefined passageways.

9. A system for detecting and correcting an existence of one or more distortions in an electromagnetic field created using a magnetic tracking device for image guided surgery, wherein the one or more distortions originate from a volume of space where a medical procedure using the magnetic tracking device is to be performed and decrease an accuracy of the magnetic tracking device, the system comprising:

a magnetic tracking device that tracks a position and orientation for each of one or more position indicating elements relative to a frame of reference of the magnetic tracking device; and a rigid object that includes a plurality of known locations, wherein for each of the plurality of known locations, baseline position and orientation information is known prior to first use of the accuracy device relative to a frame of reference of the rigid object in an undistorted volume, wherein the rigid object is placed, prior to performing a medical procedure on a patient, into the volume of space where the medical procedure is to be performed, and the one or more position indicating elements are positioned at one or more of the plurality of known locations to produce sampled position and orientation information regarding one or more of the position indicating elements in the frame of reference of the magnetic tracking device, wherein the magnetic tracking device and the rigid object enable determination of the existence of the one or more distortions in the electromagnetic field originating from the volume of space and imposed upon the one or more known points, whereby the decrease in the accuracy of the magnetic tracking device resulting from the one or more distortions is at least partially correctable based on the determination when the medical procedure using the magnetic tracking device is performed.

10. The system of claim 9, further comprising means for comparing the baseline position and orientation information of one or more of the plurality of known locations to the sampled position and orientation information of the one or more position indicating elements to determine the existence of the one or more distortions imposed upon the plurality of known locations.

11. The system of claim 10, further comprising:

means for calculating a correction map, based on the comparison, that characterizes the one or more distortions; and means for adjusting the magnetic tracking device according to the correction map.

12. The system of claim 9, further comprising means for registering the sampled position and orientation information to the frame of reference of the rigid object.

13. The system of claim 9, wherein the rigid object further comprises one or more predefined passageways within the rigid object, wherein the one or more predefined passageways are configured to receive the one or more position indicating elements and allow traversal of the one or more predefined passageways by the one or more position indicating elements, and to allow sampled position and orientation information to be obtained as the one or more predefined passageways are traversed by the one or more position indicating elements.

14. The system of claim 9, wherein the rigid object further comprises:
one or more predefined passageways within the rigid object, wherein the one or more predefined passageways are configured to receive the magnetic tracking device and allow traversal of the one or more predefined passageways by the magnetic tracking device, and to allow sampled position and orientation information to be obtained as the one or more predefined passageways are traversed by the magnetic tracking device.

15. A system for detecting and correcting an existence of one or more distortions in an electromagnetic field created using a magnetic tracking device for image guided surgery, wherein the one or more distortions originate from a volume of space where a medical procedure using the magnetic tracking device is to be performed and decrease an accuracy of the magnetic tracking device, the system comprising:
a magnetic tracking device that tracks a position and orientation for each of two or more position indicating elements relative to a frame of reference of the magnetic tracking device;
a rigid object that includes a plurality of known locations, wherein for each of the plurality of known locations, baseline position and orientation information is known relative to a frame of reference of the rigid object, wherein the rigid object is placed into the volume of space and the two or more position indicating elements are positioned at one or more of the plurality of known locations to obtain sampled position and orientation information regarding two or more of the position indicating elements in the frame of reference of the magnetic tracking device, wherein the sampled position and orientation information is obtained for the two or more position indicating elements relative to one another; and
one or more computing systems coupled to the magnetic tracking device configured to:
compare the baseline position and orientation information of one or more of the plurality of known locations to the sampled position and orientation information of at least one of the two or more position indicating elements; and
determine the existence of the one or more distortions in the electromagnetic field that originated from the volume of space and that are imposed upon the one or more of the plurality of known locations based on the comparison, whereby the decrease in the accuracy of the magnetic tracking device resulting from the one or more distortions is at least partially correctable based on the determination when the medical procedure using the magnetic tracking device is performed.

16. A method for detecting and correcting an existence of one or more distortions in an electromagnetic field created using a magnetic tracking device for image guided surgery, wherein the one or more distortions originate from a volume of space where a medical procedure using the magnetic tracking device is to be performed and decrease an accuracy of the magnetic tracking device, the method comprising:
placing a rigid object into a known undistorted volume, wherein the rigid object comprises one or more position indicating elements at one or more known locations of the rigid object, and wherein the one or more position indicating elements are associated with baseline position and orientation information that indicates known position and orientation of the one or more known locations prior to first use of the rigid object;
obtaining measured position information of the one or more position indicating elements relative to a frame of reference of the magnetic tracking device in the known undistorted volume;
registering the measured position information to a frame of reference of the rigid object;
comparing the measured position information to the baseline position information;
placing, prior to performing the medical procedure, the rigid object into the volume of space when a difference between the measured position information and the baseline position information does not exceed a predetermined threshold;
obtaining experimental position information of the one or more position indicating elements relative to a frame of reference of the magnetic tracking device in the volume of space;
registering the experimental position information to the frame of reference of the rigid object;
comparing the experimental position information to the baseline position information;
determining the existence of the one or more distortions in the electromagnetic field that originated from the volume of space and that are imposed upon the one or more known locations when a difference between the experimental position information and the baseline position information exceeds a predetermined threshold;
characterizing the one or more distortions based on the comparing;
creating a correction map that enables adjustment of the magnetic tracking device to correct for the one or more distortions originating from the volume of space; and
adjusting the tracking device according to the correction map.

17. A method for detecting and correcting an existence of one or more distortions in an electromagnetic field created using a magnetic tracking device for image guided surgery, wherein the one or more distortions originate from a volume of space where a medical procedure using the magnetic tracking device is to be performed and decrease an accuracy of the magnetic tracking device, the method comprising:
receiving, by one or more computer systems, sampled position and orientation information of one or more position indicating elements positioned at one or more known locations of a rigid object when the rigid object is placed into the volume of space prior to the medical procedure, wherein the one or more position indicating elements are associated with baseline position and orientation information that indicates known position and orientation of the one or more known locations prior to first use of the rigid object;
comparing, by the one or more computer systems, the sampled position and orientation information to the baseline position and orientation information; and
determining, by the one or more computer systems, the existence of the one or more distortions in the electromagnetic field originating from the volume of space and imposed upon the one or more known locations based on the comparison, whereby the decrease in the accuracy of the magnetic tracking device resulting from the one or more distortions is at least partially correctable based on the determination.

18. The method of claim 17, the method further comprising:
characterizing the one or more distortions in the volume of space when a difference between the sampled position and orientation information and the baseline position and orientation information exceeds a predetermined threshold;
creating a correction map, based on the characterizing, that enables adjustment of the magnetic tracking device to correct for the one or more distortions in the volume of space; and
adjusting the magnetic tracking device according to the correction map.

19. The method of claim 17, further comprising:
registering the sampled position and orientation information to a frame of reference of the rigid object.

20. The method of claim 19, further comprising:
monitoring, while the medical procedure is being conducted, the volume of space for distortions by periodically obtaining additional sampled position and orientation information and comparing the additional sampled position and orientation information to the baseline position and orientation information.

21. The method of claim 19, further comprising:
dynamically referencing, while the medical procedure is being conducted, at least a portion of a subject of the medical procedure using the one or more position indicating elements.

22. The method of claim 21, wherein a dynamic reference for use during said dynamically referencing is the rigid object.

23. The method of claim 17, wherein each of the one or more position indicating elements are connected to a multiplexer, and wherein the sampled position and orientation information is obtained by the magnetic tracking device via cycling through the one or more position indicating elements using the multiplexer.

24. The method of claim 17, wherein the rigid object rigid object further comprises one or more predefined passageways within the rigid object, wherein the one or more predefined passageways are configured to receive the one or more position indicating elements and allow traversal of the one or more predefined passageways by the one or more position indicating elements, and to allow sampled position and orientation information to be obtained as the one or more predefined passageways are traversed by the one or more position indicating elements.

25. A rigid object device for detecting and correcting an existence of one or more distortions in an electromagnetic field created using a magnetic tracking device for image guided surgery, wherein the one or more distortions originate from a volume of space where a medical procedure using the magnetic tracking device is to be performed and decrease an accuracy of the magnetic tracking device, the rigid object device comprising:
one or more position indicating elements positioned at one or more known locations of the rigid object, wherein the one or position indicating elements are associated with baseline position and orientation information that indicates known position and orientation of the one or more known locations prior to first use of the rigid object,
wherein the one or more position indicating elements are configured to facilitate obtaining sampled position and orientation information of the one or more position indicating elements when the rigid object is placed into the volume of space prior to the medical procedure, and
wherein a comparison of the sampled position and orientation information with the baseline position and orientation information enables a determination that the one or more distortions in the electromagnetic field originating from the volume of space and imposed upon the one or more known locations based on the comparison exist in the volume of space.

26. The rigid object device of 25, further comprising:
one or more predefined passageways within the rigid object, wherein the one or more predefined passageways are configured to receive a magnetic tracking device and allow traversal of the one or more predefined passageways by the magnetic tracking device, and to allow sampled position and orientation information to be obtained as the one or more predefined passageways are traversed by the magnetic tracking device.

27. The system of claim 26, wherein the one or more predefined passageways are made using a rapid prototyping process chosen from one of selective laser sintering (SLS), stereolithography (SLA), or 3D printing.

28. A method of detecting and correcting an existence of one or more distortions in an electromagnetic field created using a magnetic tracking device for image guided surgery, wherein the one or more distortions originate from a volume of space where a medical procedure using the magnetic tracking device is to be performed and decrease an accuracy of the magnetic tracking device, the method comprising:
detecting, by one or more processors of the magnetic tracking device, sampled position and orientation information of one or more position indicating elements positioned at one or more known locations of a rigid object when the rigid object is placed into the volume of space prior to the medical procedure,
wherein the one or more position indicating elements are associated with baseline position and orientation information that indicates known position and orientation of the one or more known locations prior to first use of the rigid object; and
transmitting to one or more computer systems coupled to the magnetic tracking device the sampled position and orientation information.

29. The method of claim 28, said detecting further comprising:
detecting the sampled position and orientation information as the magnetic tracking device is traversed through one or more predefined passageways within the rigid object.

30. The method of claim 2, further comprising:
conducting the medical procedure in the volume of space after the rigid object that has been used to characterize the distortion has been removed from the volume of space.

31. A rigid object device for detecting and correcting an existence of one or more distortions in an electromagnetic field created using a magnetic tracking device for image guided surgery, wherein the one or more distortions originate from a volume of space where a medical procedure using the magnetic tracking device is to be performed and decrease an accuracy of the magnetic tracking device, the rigid object device comprising:
one or more known locations of the rigid object, wherein the one or more known locations are associated with baseline position and orientation information that indicates known position and orientation of the one or more known locations prior to first use of the rigid object, wherein the one or more known locations are configured to facilitate obtaining sampled position and orientation information of the one or more known locations when the rigid object is placed into the volume of space prior to the medical procedure, and wherein a comparison of the sampled position and orientation information with the baseline position and orientation information enables a determination that the one or more distortions in the electromagnetic field originating from the volume of space and imposed upon the one or more known locations based on the comparison exist in the volume of space, whereby the decrease in the accuracy of the magnetic tracking device resulting from the one or more distortions is at least partially correctable based on the determination.

32. The rigid object device of 31, further comprising:

one or more predefined passageways within the rigid object, wherein the one or more predefined passageways are configured to receive one or more position indicating elements and allow traversal of the one or more predefined passageways by the one or more position indicating elements, and to allow sampled position and orientation information to be obtained as the one or more predefined passageways are traversed by the one or more position indicating elements.

* * * * *